United States Patent [19]

Baker et al.

[11] Patent Number: 5,730,857

[45] Date of Patent: Mar. 24, 1998

[54] METHOD FOR DETECTING IONS AND SMALL MOLECULES IN AQUEOUS AND NON-AQUEOUS LIQUIDS

[75] Inventors: Mark D. Baker, Bramalea; Chandana Senaratne, Guelph, both of Canada

[73] Assignee: University of Guelph, Ontario, Canada

[21] Appl. No.: 255,734

[22] Filed: Jun. 7, 1994

Related U.S. Application Data

[62] Division of Ser. No. 235,212, Apr. 29, 1994, abandoned, which is a continuation of Ser. No. 833,710, Feb. 11, 1992, abandoned.

[30] Foreign Application Priority Data

Feb. 13, 1991 [GB] United Kingdom ................... 9103053

[51] Int. Cl.$^6$ ................................................. G01N 27/26
[52] U.S. Cl. ........................ 205/775; 204/412; 205/788; 205/789; 205/789.5
[58] Field of Search .......................... 204/153.2, 153.22, 204/153.1, 416–419, 430

[56] References Cited

U.S. PATENT DOCUMENTS

| | | | |
|---|---|---|---|
| 2,614,976 | 10/1952 | Patnode et al. | 204/418 |
| 3,839,162 | 10/1974 | Ammer | 204/420 |
| 3,856,633 | 12/1974 | Fletcher, III | 204/419 |
| 3,865,708 | 2/1975 | Light et al. | 204/409 |
| 4,422,917 | 12/1983 | Hayfield | 204/196 |
| 4,440,602 | 4/1984 | Dobson | 204/416 |
| 4,944,273 | 7/1990 | Baresel et al. | 204/424 |

OTHER PUBLICATIONS

Talanta, 1991, vol. 38, No. 1. pp. 27–35, Analytical Implications of Zeolites In Overlayers At Electrodes, Debra R. Rolison, Robert J. Nowak, Timothy A. Welsh and Catherine G. Murray. Month unavailable.

Anal. Chem., 1985, vol. 57, pp. 2739–2740 Voltammetric Determination of Nonelectroactive Ions At a Modified Electrode, James A. Cox, Basudev K. Das. Month unavailable.

Anal. Chem., Dec. 1, 1989, vol. 61, No. 23, pp. 2594–2598, Amperometric Detection of Nonelectroactive Cations In Flow Systems At a Cupric Hexacyanoferrate Electrode, Karsten N. Thomsen, Richard P. Baldwin.

Analytica Chimica Acta, 1988, vol. 207, pp. 95–102, Accumulation And Voltammetric Measurement of Silver At Zeolite–Containing Carbon–Paste Electrodes, Joseph Wang, Teddy Martinez. Month unavailable.

(List continued on next page.)

*Primary Examiner*—T. Tung

[57] ABSTRACT

Provided is a method and apparatus for detecting electroinactive ions, and electroinactive ions solvated by small molecules including water. The method and apparatus utilizes a microporous ion exchange material such as a zeolite containing initially an electroactive species contained within the pores. The method operates on the principle that when charged species present in solution can access the pores of the microporous material, an ion-exchange reaction will occur whereupon the electroactive species will exit the microporous material, being replaced by the charged species. The electroactive species, upon exiting the microporous material, undergoes electrochemical reduction or oxidation at an electrode having a sufficiently high potential applied thereto. The method and detector disclosed herein is size selective since for example zeolites with a pore size comparable to that of the solvated ion to be detected but smaller than other electrolyte components can be utilized. In addition to being used as an ion detector per se, the detector may be used for detecting trace amounts (sub parts per million) of water in non-aqueous media by using the fact that hydrated cation species can readily access the zeolite interior via the pore network thus expelling an electroactive ion into solution. In contrast, the same cation when solvated by organic molecules will be size excluded from the zeolite. The detector can be utilized for the detection of other small molecules using the same principle provided that they form a solvated complexes with electrolyte cations which are not size excluded from the zeolite.

8 Claims, 8 Drawing Sheets

OTHER PUBLICATIONS

Abstract L1 Answer 5 of 36, AU: Nagai, Masayuki; Hibino, Masayuki, Nishino, Tadashi, Humidity Sensor Characteristics of Porous Zeolite Ceramics At Elevated Temperatures.

Abstract L1 Answer 9 of 36, Chemical Sensor.

Abstract L1 Answer 14 of 36, AU: Uchikawa, Hidefusa, Manufacture of Moisture Sensitive Materials.

Abstract L1 Answer 19 of 36, Zeolite Humidity Sensors.

Abstract L1 Answer 28 of 36, Moisture Sensor.

Abstract L1 Answer 29 of 35, Moisture Sensor.

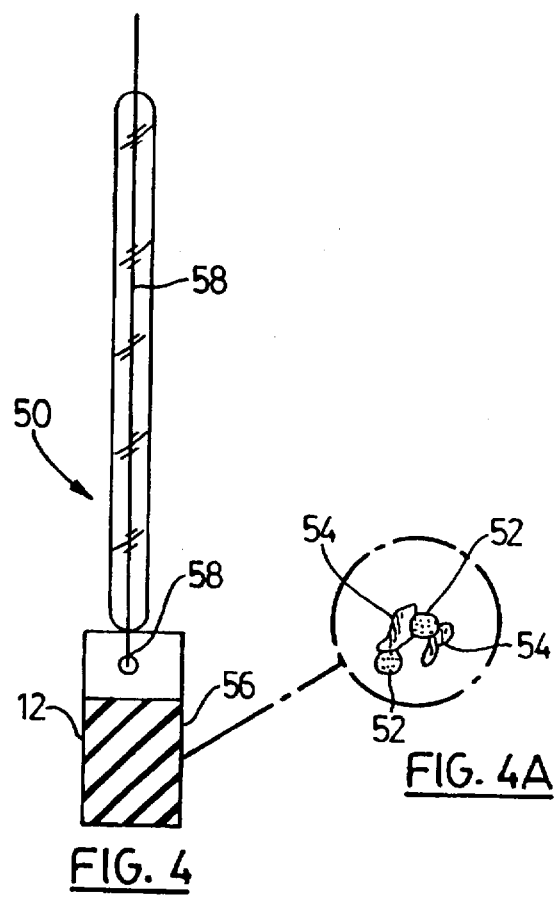
FIG. 4
FIG. 4A
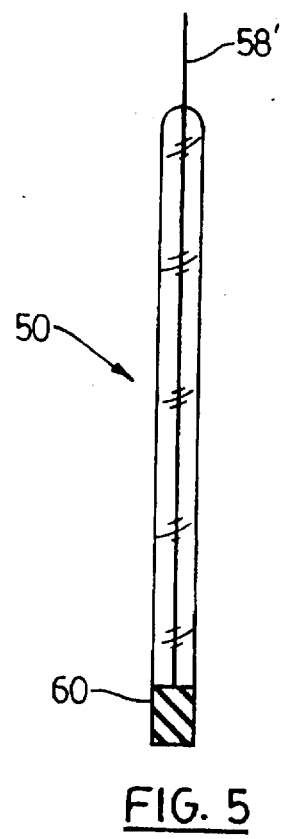
FIG. 5
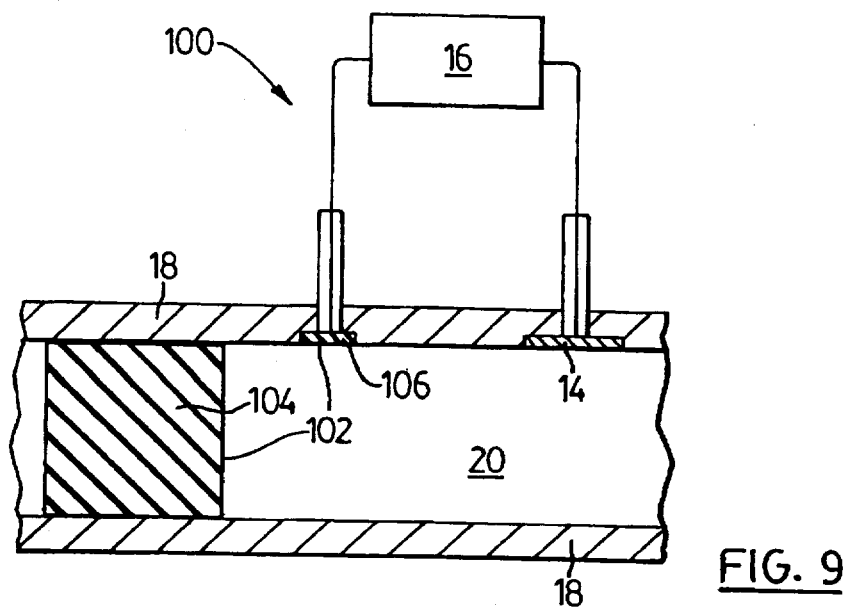
FIG. 9

METHOD FOR DETECTING IONS AND SMALL MOLECULES IN AQUEOUS AND NON-AQUEOUS LIQUIDS

The present application is a divisional application of U.S. patent application Ser. No. 08/235,212 filed on Apr. 29, 1994, now abandoned, which is a continuation of Ser. No. 07/833,710 filed on Feb. 11, 1992, now abandoned, entitled "Solution Phase Ion and Water Sensitive Detector".

FIELD OF THE INVENTION

The present invention relates generally to a method for detecting ions and small molecules in aqueous and non-aqueous liquids.

BACKGROUND OF THE INVENTION

Solution phase ion detectors form an integral part of certain analytical procedures, one important application being ion chromatography. Indeed, as an analytical technique ion chromatography did not really make an impact until relatively recently (1975) when a viable solution phase ion detector was developed. This ion chromatograph, marketed by Dionex Corporation, uses a conductometric based universal ion detector. Since conductivity is a bulk property measurement, it is by itself not capable of good sensitivity since the mobile phases used in ion chromatography are highly conducting and the conductivity of the species being detected is a small fraction of the overall solution conductivity thereby giving rise to a significant dynamic range problem.

One method of overcoming this problem is to employ a chemical suppression technique wherein the eluent conductivity is decreased while the analyte conductivity is increased thereby increasing the signal contrast above the background. While chemical suppression techniques give a superior detection limit (roughly an order of magnitude), the technique is not applicable to many materials including heavy metals and organics to mention a few.

Other detection techniques such as direct electrochemical detection cannot be universally applied as an aqueous ion detector since the reduction potentials of many cations lie outside the electrochemical stability region of water.

The specific sensing of water in organic solvents is deemed important in the monitoring of industrial feedstocks. In this area, interference (i.e. non-selective responses) has been a severe problem. In addition, the detection of water in organic solvents is deemed important in chemical laboratories. Karl Fisher titration systems are currently available for this application and have detection limits in the vicinity of about 1 ppm.

SUMMARY OF THE INVENTION

The method and detector of the present invention utilizes an electrochemical detection technique, whereby both organic and inorganic species may be detected. The detector is not limited in scope by the reduction or oxidation potentials of these species in contrast to the detectors previously used.

The present invention provides a method for detecting electroinactive ions or electroinactive ions solvated by small molecules in liquid samples. The method comprises the steps of providing a liquid sample to be tested for electroinactive ions or small molecules and contacting said liquid sample with an ion exchange material having pores of predetermined molecular dimensions for restricting access to the pores on the basis of size. The pores initially contain electroactive ions within the pores, whereby at least some of the electroactive ions are released into the liquid sample from said pores by ion exchange with electroinactive ions or electroinactive ions solvated by small molecules when the electroinactive ions or electroinactive ions solvated by small molecules can access the pores on the basis of size. The liquid sample containing the electroactive ions is brought into contact with an electrode after the liquid sample has contacted the ion exchange material. A bias potential is then applied to the electrode with respect to a counter-electrode whereby the bias potential is sufficient to cause an electrochemical reaction between the electroactive species and the electrode to produce an electrical current. The electrical current resulting from the electrochemical reaction is recorded and related to the concentration of the electroinactive ions initially in the liquid sample.

In another aspect of the invention there is provided a method for detecting small molecules in organic solvents comprising organic molecules and electroinactive ions. The small molecules are generally smaller than the organic molecules and the method includes the steps of providing a sample of an organic solvent to be tested for small molecules contained therein and contacting the sample with a zeolite. The zeolite has pores of molecular dimensions effective for restricting access to the pores on the basis of size and the pores initially contain electroactive ions. At least some of the electroactive ions are released into the sample from the pores by ion exchange with electroinactive ions solvated by small molecules when the electroinactive ions solvated by small molecules can access the pores on the basis of size. Thereafter the sample containing the electroactive ions is brought into contact with an electrode and a bias potential is applied to the electrode with respect to a counter-electrode whereby the bias potential is sufficient to cause an electrochemical reaction between the electroactive species and the electrode to produce an electrical current which is then recorded.

BRIEF DESCRIPTION OF THE DRAWINGS

The method of the present invention will now be described, by way of example only, with respect to the following drawings, in which:

FIG. 4 is an elevational view of a zeolite/carbon/polystyrene composite detector electrode showing detail of the composite electrode;

FIG. 4A is an enlargement of a portion of the electrode of FIG. 4;

FIG. 5 is an elevational view of a zeolite/epoxy bonded graphite composite detector electrode;

FIG. 9 is a diagrammatic view of an alternative embodiment of the detector electrode;

DETAILED DESCRIPTION OF THE INVENTION

Figure 1:
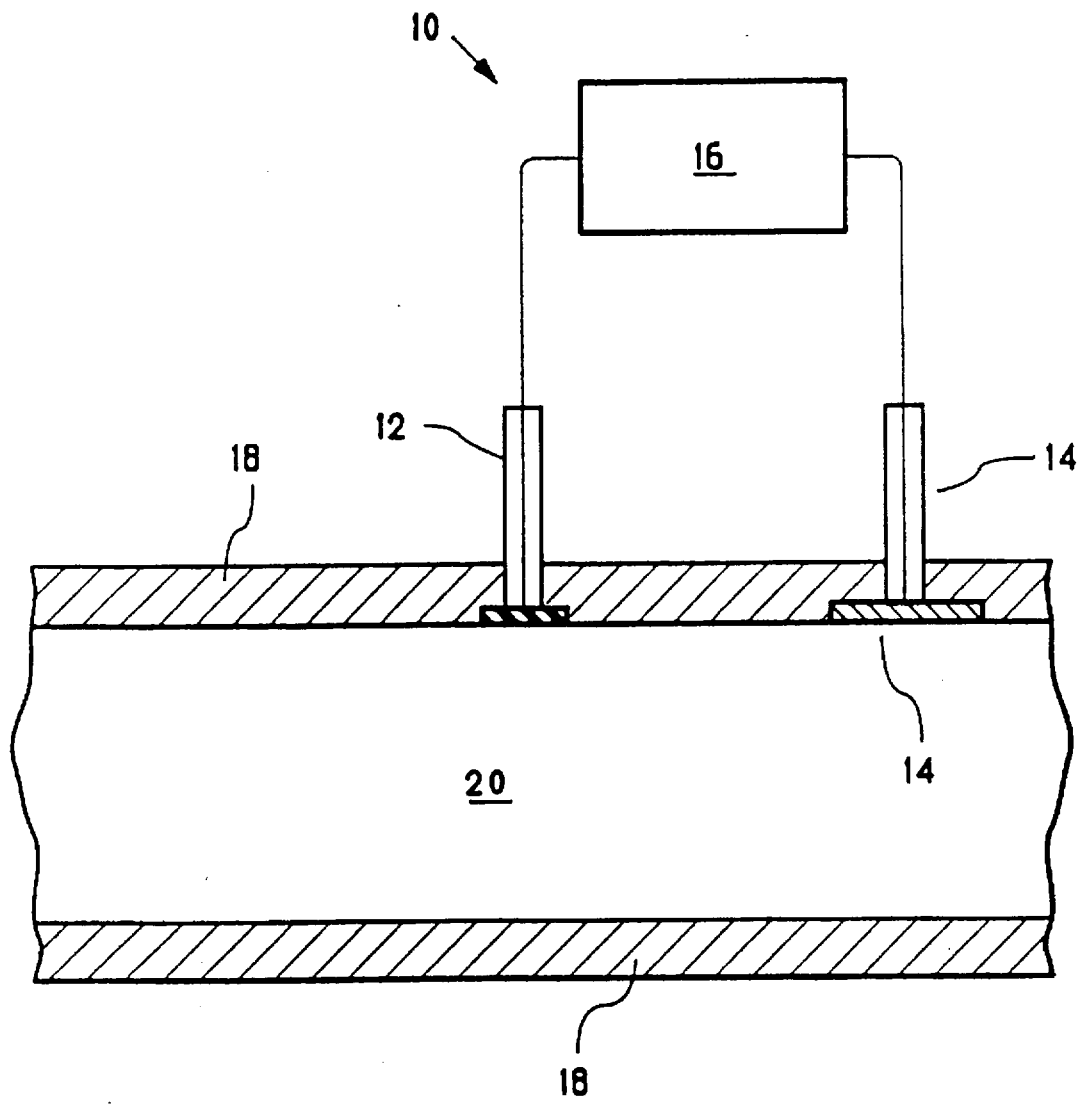
FIG. 1 is a diagrammatic view of a detector embodying the subject invention.

Referring first to FIG. 1, an ion and small molecule detector 10 comprises a zeolite based detector electrode 12 and a suitable counter electrode 14 both electrically coupled to a potentiostat 16. Electrodes 12 and 14 are shown mounted in the side wall of a liquid flow (or static) system 18. Solution 20 is the solution being tested and may be an aqueous or non-aqueous medium. Although this embodiment of the detector shows a two electrode configuration, it will be appreciated by those skilled in the art that three electrode configurations employing a reference electrode are routinely employed for providing potential control of the detector electrode.

Figure 2:
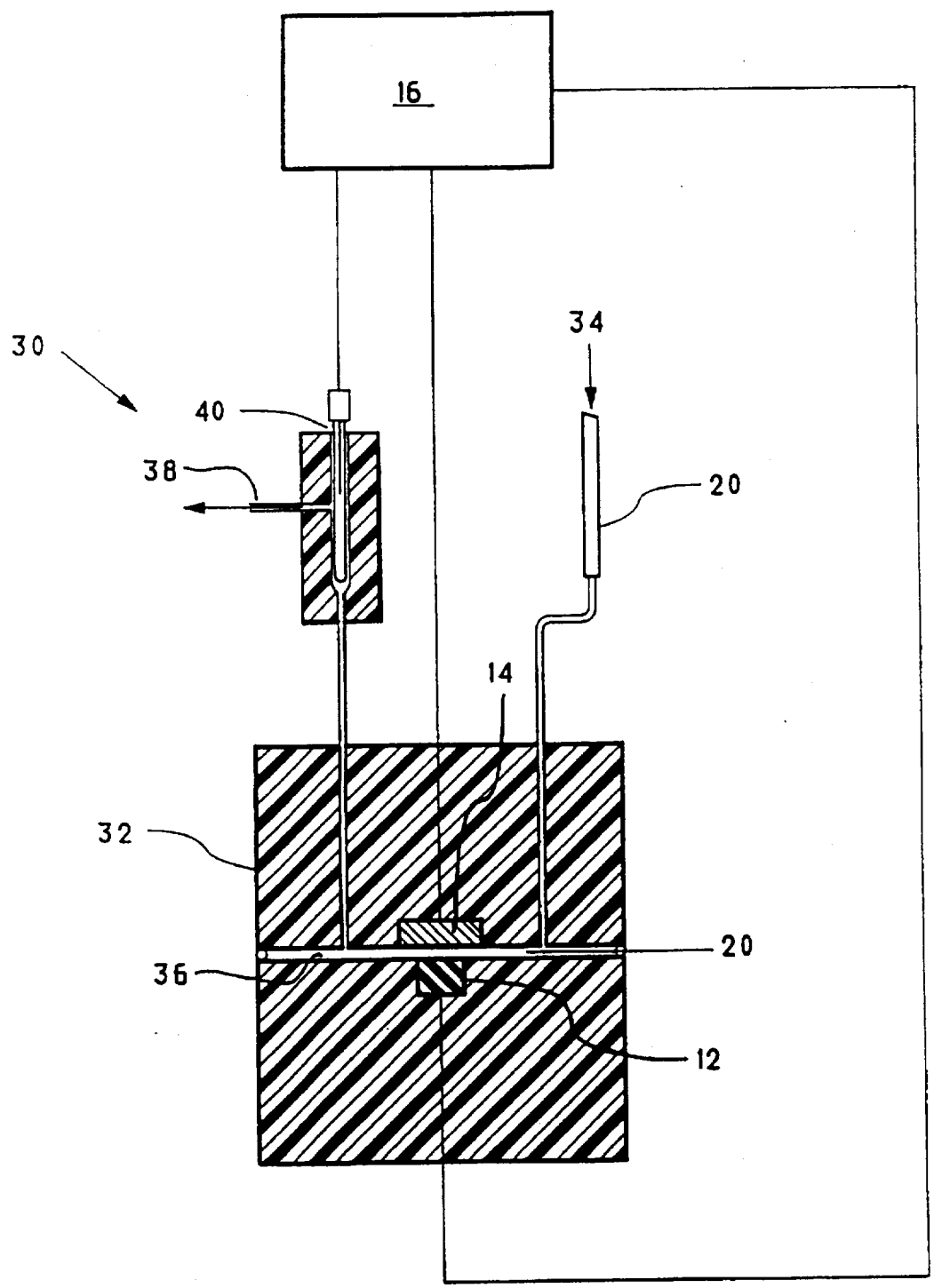
FIG. 2 is a diagrammatic view of an alternative embodiment of the detector.

FIG. 2 illustrates an alternative view of a detector 30 of the present invention. Detector 30 comprises zeolite based detector electrode 12 but now adapted to be inserted into a commercially available electrochemical detector housing 32 utilized in liquid chromatography. A solution inlet 34 admits solution 20 into a channel 36 containing detector electrode 12 and counter electrode 14 in an adjacently spaced relation. Solution 20 is flowed between electrodes 12 and 14 to exit detector 30 at an exit port 38. Detector 30 is provided with a reference electrode 40 located adjacent exit port 38. Detector electrode 12, counter electrode 14 and reference electrode 40 are electrically coupled to potentiostat 16.

Figure 3:
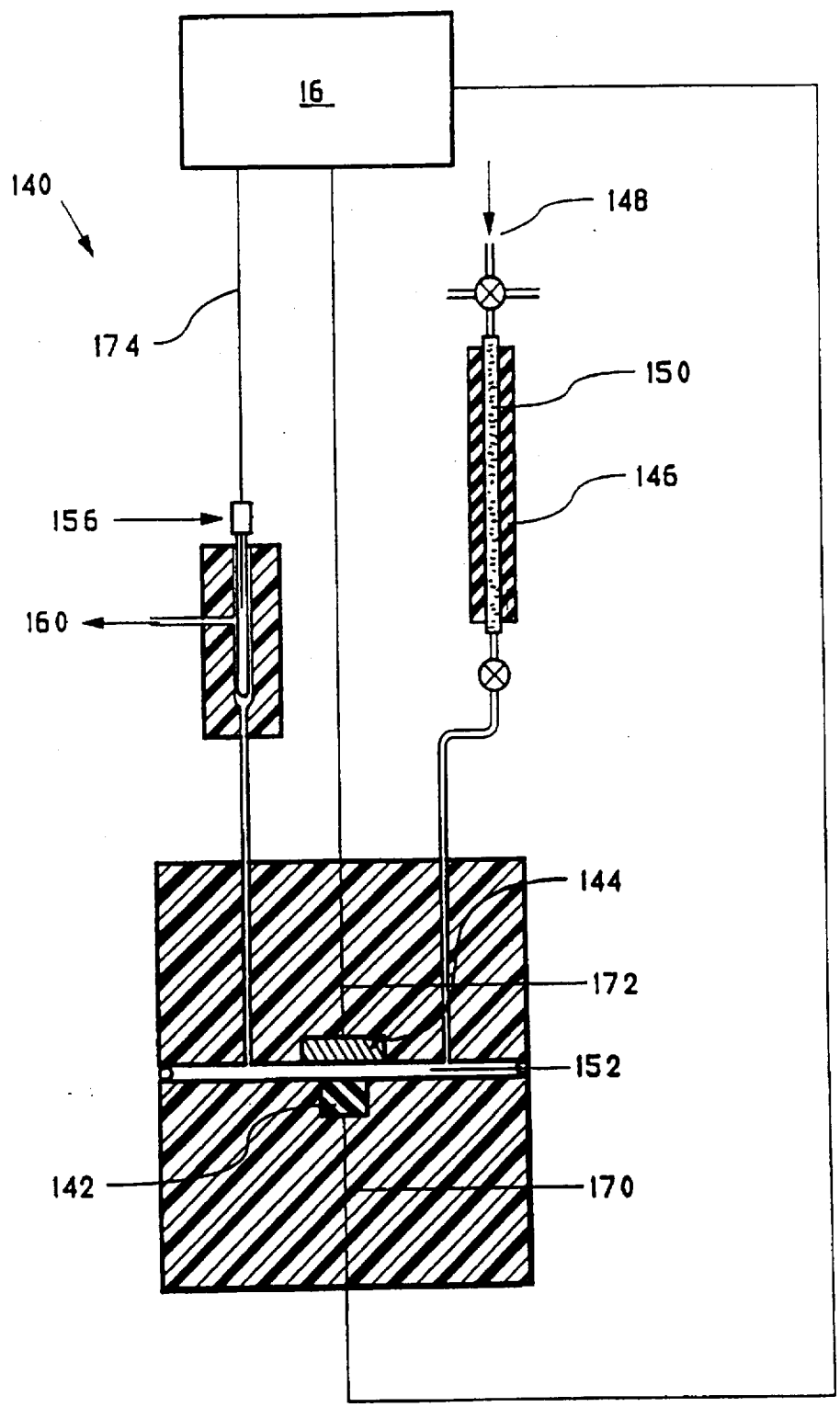
FIG. 3 is a diagrammatic view of yet another embodiment of the detector.

Referring to FIG. 3, another embodiment of a detector is shown generally at 140 and includes a conducting detector electrode 142, a counter electrode 144 plus a zeolite column 146. A solution inlet 148 admits solution 150 into zeolite column 146. Ion exchange occurs in the column and the solution containing the metal species then enters channel 152 and passes between electrodes 142 and 144. Detector 140 is provided with a reference electrode 156 located adjacent a solution exit port 160. Conducting electrode 142, counter electrode 144 and reference electrode 156 are coupled to potentiostat 16 via wires 170, 172 and 174 respectively.

Referring to FIG. 4 and FIG. 4A, the structure and fabrication of a detector electrode 50 similar to composite electrode 12 will now be described. Electrode 50 comprises an intimate mixture of a zeolite component 52 and a chemically inert and electrically conductive material 54, see the blowup in FIG. 4A. This mixture can be immobilized on a conductive substrate 56 using a binder component (not shown). Contained within the interior pores of zeolite component 52 are an electroactive species (not shown). Electrical contact is made to electrode 50 with an electrically conducting wire 58.

The criteria for conductive component 54 is that it be chemically inert in the medium of use. The binder component may be chosen from a wide variety of chemically stable and inert polymer binders such as polystyrene, teflon™, various epoxies, KEL-F™ and polythene to mention just a few. As described above, the binder and conductor are separate components which are mixed with the zeolite component to give a composite electrode. Alternatively, the binder and conductor may be in a prefabricated or pre-mixed form, such a epoxy bonded graphite. FIG. 5 illustrates an alternative embodiment of detector electrode 50 wherein the zeolite and conductive component mixture shown at 60 are formed by mixing the zeolite with an epoxy bonded graphite. Note that the binder components previously mentioned could also be used in this embodiment. Also, the manner in which electrical contact is made to the zeolite/binder composite 60 can either be by direct electrical contact or by using a conductive mercury pool, silver epoxy or other metal containing epoxies.

Figure 6:
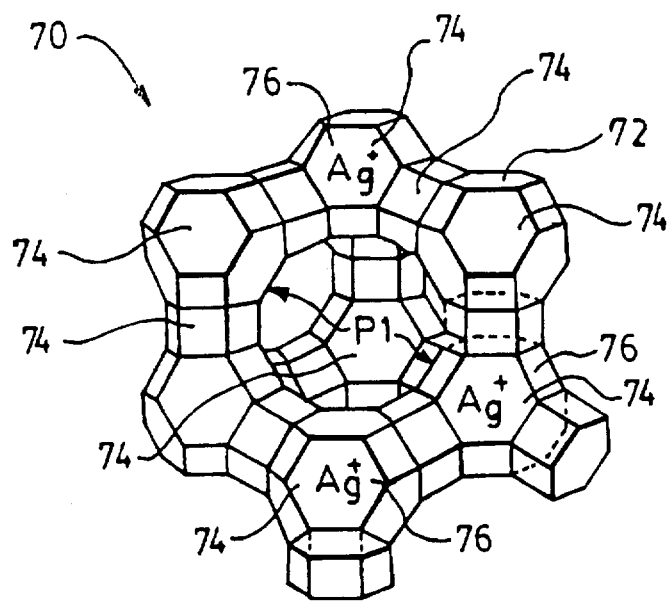
FIG. 6 is a schematic perspective view of the framework structure of zeolite Y.

The principle on which the zeolite based solution phase ion and small molecule detector device of the subject invention works is as follows. The zeolite family of materials are microporous, crystalline solids having well defined pore diameters. Different species of zeolite have different crystal structures and different pore diameters. Referring to FIG. 6, there is shown a zeolite species 70 (usually referred to as zeolite Y) from the zeolite family of materials having a framework 72, cages 74, and a well defined pore diameter P1. Since the zeolite is an aluminosilicate, framework 72 possesses a negative charge, thus during synthesis a charge balancing counter ion such as $Na^+$ or $K^+$ is incorporated into the cages (not shown). An electroactive species 76 (shown as $Ag^+$) is incorporated into cages 74 of the zeolite either before or after fabrication of the detector electrode using a known technique, e.g. ion-exchange. As will be discussed below, it is not necessary that a complete ion-exchange occurs for the detector to work effectively.

The term "electroactive ion" refers to ions that can be either electrochemically oxidized or reduced in the liquid solution of interest, in other words the reversible potential of the species lies within the stability range of the solution. The electroactive species which is incorporated into the zeolite may be chosen from a large number of metals including but not restricted to silver (Ag), copper (Cu), nickel (Ni), cobalt (Co) and manganese (Mn) to mention just a few. The criteria to be considered in the selection of the electroactive species is that it be easily ion-exchanged into and out of the zeolite and that it be readily reduced or oxidized in the electrolyte of interest.

The term "electroinactive ion" refers to ions that cannot be oxidized or reduced within the stability region of the electrolyte. The zeolite based ion detector can be used to detect ions not normally amenable to direct amperometric detection, e.g. alkali metals since the reversible potentials of these species lie outside the stability region of most aqueous solutions. In this context, electroinactive also refers to metal species which have reduction or oxidation potentials within the stability region of the electrolyte but have high overpotentials on the composite electrode so that they do not undergo electrochemical reaction at any significant rate within the stability region of the electrolyte. In addition, ions other than "electroinactive ions" defined above may be determined. Specifically, ions that are reducible or oxidizable (within the stability region of the electrolyte) but at potentials outside of that of the detector electrode (set by the potentiostat). The DC potential applied to the detector electrode is not cathodic or anodic enough to directly reduce or oxidize the ion of interest. Also, solution phase ions that are oxidized or reduced at the potential of the detector electrode can be determined indirectly using calibration curves.

Referring to FIGS. 1, 2 and 4-6, in operation the species present in solution 20 (hereinafter referred to as the analyte species or analyte ion) can be determined amperometrically when the electroactive species 76 is either reduced (or oxidized) at a site on a conductive portion of composite electrode 12. For this to occur electroactive species 76 must exit zeolite cage 74 and once on the surface of conducting portion 54 of electrode 12 it can be either reduced or oxidized. For electroactive species 76 to leave the zeolite cage it must be replaced by analyte species from solution 20 in order to maintain charge neutrality on zeolite 70. This replacement occurs by ion-exchange. Therefore the analyte species exchanging with the electroactive species must be capable of accessing interior cages via the zeolite pores.

The detector illustrated in FIG. 3 operates on the same principle except that the ion exchange reaction takes place in zeolite column 146 and the liberated electroactive species flows in solution past conducting electrode 142.

The following steps are involved in the method disclosed herein for detecting an analyte ion in aqueous or non-aqueous solution.

i. Solvated analyte cation ion-exchanges with electroactive cation in the zeolite;

ii. electroactive cation exits the zeolite pore and diffuses across electrode surface to a conductive site; and iii. electroactive cation oxidized or reduced depending on the electrode potential. Current flowing due to reduction or oxidation is recorded and used to determine concentration of analyte species.

These reaction steps may be represented in the following way, using $Ag^+$ as the electroactive component and $K^+$ as the analyte species being detected:

$K^+$ solvated→$K^+$ zeolite $Ag^+$ zeolite→$Ag^+$ solution $Ag^+$ solution+$e^-$→Ag Thus while the electrochemical current is due to the reduction (or oxidation) of the electroactive species, the magnitude of this current is controlled by the concentration of the analyte species in solution. That is, by the rate of ion-exchange between electroactive and analyte species.

Since the zeolites have well defined pore sizes, if the solvated cation from the electrolyte is too large to enter the zeolite pores then electroactive species 76 cannot exit the zeolite. Thus no electrochemical reaction will occur and zero Faradaic current will be detected. Since there are a large number of zeolite materials having a broad range of pore diameters, the detector may therefore be designed for size selective detection of the solution phase species. Specifically, size sensitivity may be achieved by utilizing zeolites having a pore size comparable to the size of the solvated ion of interest while excluding larger species.

Note that the detector electrode described herein can also be used to determine one component of a multi-component system providing that the zeolite pore size is matched to the component of interest. An alternative mechanism whereby this can occur where two components can enter the zeolite is through preferential adsorption of one component which has been observed and reported in the open literature.

Figure 7:
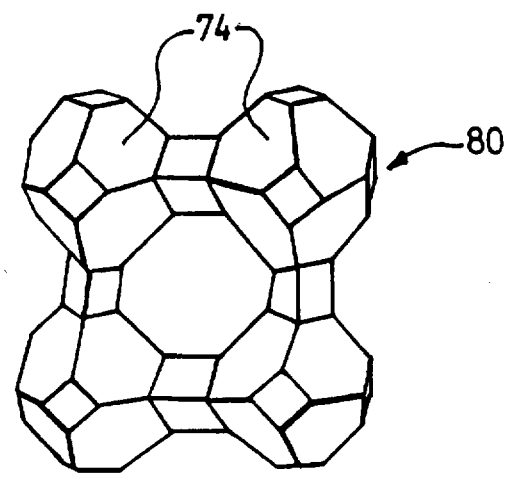
FIG. 7 is a perspective diagrammatic view of the framework structure of zeolite A.

FIG. 7 shows another zeolite type, known as zeolite A at 80.

Figure 8:
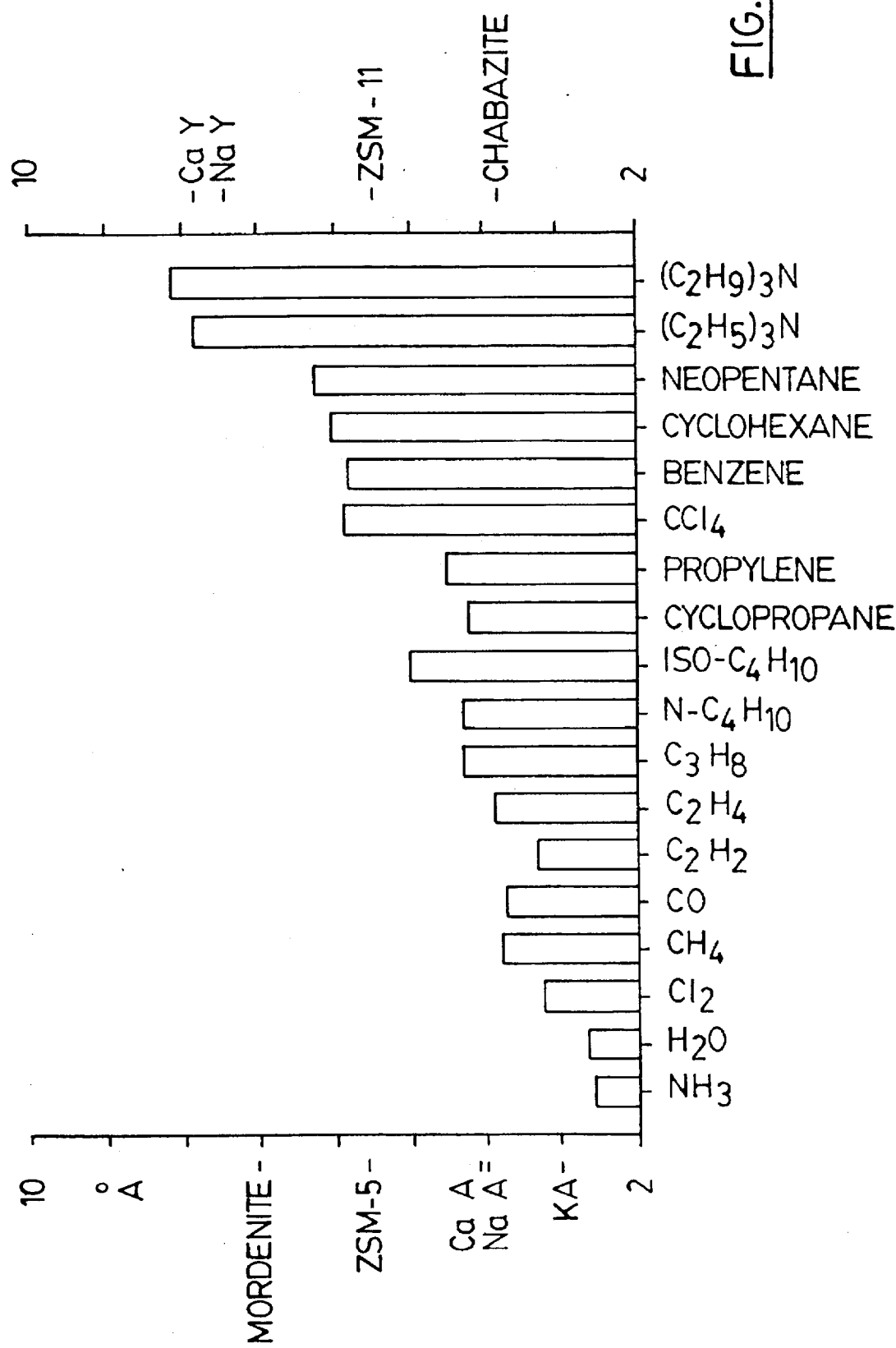
FIG. 8 is a representation of the pore sizes of various zeolite types compared with the kinetic diameters of some common molecules.

Referring to FIG. 8, the pore sizes of various zeolite types are compared with the kinetic diameters of various analyte species.

The suppression of any current due to the absence in solution of a small electrolyte ion (that is not size excluded from the zeolite) is of great importance. This is an attractive feature of the detector since the mobile phase used in ion chromatography is an electrolyte solution. Any current flowing due to this ion which is at a very high concentration could swamp the response of the detector. Thus the detector circumvents the dynamic range problems described earlier.

The size selectivity of the detector electrode of the present invention may be considered to form the basis of a size selective background current suppression technique whereby small concentrations of analyte ions may be readily detected in a sea of background size excluded electroinactive and electrolyte ions.

The presence of electroactive impurity cations in the solution of interest having reversible potentials within the stability range of the electrolyte in addition to good kinetics for oxidation or reduction may also lead to swamping of the detector if they are present at high enough concentration. This is because direct oxidation or reduction of the impurity species on the conductive portion of the electrode may be possible with current magnitudes greater than those achievable by reaction of the electroactive species from the zeolite. One way to avoid this potential problem is to incorporate a "poison" into the composite electrode which serves to increase the overpotential of the redox reactions of any "impurity" species present. It will be appreciated that this poison preferably has no significant effect on the kinetics of the redox reactions of the electroactive species. Another way of overcoming this potential problem may be to change to an electroactive ion which allows the use of a DC potential where the impurity ions cannot be reduced or oxidized.

In addition to being a size sensitive ion detector, the detector may also be used to detect trace amounts of water in non-aqueous solvents such as organic feedstock. In an organic solution containing cation species such as $K^+$ or $Na^+$, with no water present the cations will be solvated with organic molecules of the solvent. The size of this solvation sheath will vary depending on the size and dipole moment of the organic molecules. However, if a small amount of water is present then cations may be hydrated with water molecules if the latter have a dipole moment greater than the organic molecules. Generally, a water hydrated cation will be much smaller than the same cation having a solvation sheath comprised of organic molecules. By appropriate choice of the zeolite pore size, an organically solvated cation can be size excluded from the zeolite while the same hydrated cation can gain access to the zeolite pore whereby the cation can ion-exchange with the electroactive species with the result that an electrochemical current will be observed. In addition zeolite A is a hydrophillic material and is therefore a useful material for water detection.

It will be appreciated that the detector disclosed herein may be used for detecting other small molecules such as for propanol and methanol to mention just a few.

Referring to FIG. 9, another embodiment of the ion and small molecule detector is shown at 100 provided with a detector electrode 102 comprising a zeolite component 104 in the form of a plug or thin membrane and a separate conducting electrode component 106. Zeolite component 104 is provided with an electroactive species (not shown) and an optional binder component which acts to hold the zeolite powder together. Electrode 106 is used to amperometrically detect liberated electroactive species. Detector 100 operates on the same principle as detector 10 and the same reaction sequence is followed as described previously but with the exception that instead of liberated species diffusing to a site on zeolite portion 104, it now diffuses to conductive electrode 106 where it is reduced or oxidized and thereby amperometrically detected. Conductive electrode 106 may be fabricated from a wide variety of materials including but not restricted to Pt, Au, Hg, Ag and carbon. Detector 100 may be the preferable configuration when direct electrical contact between zeolite portion 104 and the rest of the detector 100 is not feasible. For example, composite electrode 12 of FIG. 2 is replaced by a conducting electrode while a separate zeolite portion, in the form of a plug or thin membrane, is attached to solution inlet 34.

In another alternative embodiment of the electrochemical based ion and water detector of the subject invention, the electrically conducting component, graphite powder in the examples above may be replaced by other suitable materials. Thus while carbon is preferable for many aqueous applications and non-aqueous applications, in very strong acids or bases it may be preferable to use the more chemically resistant conductive suboxide of titanium known as Ebonix*, which has the same conductivity as graphite. Other oxide based conductors may also be employed.

In still another embodiment, the insulating zeolite may be confined within a microporous, stable and electrically conducting polymer matrix. In addition to providing the desirable electrical conductivity, this polymer may also serve the role of the binder component thereby eliminating this separate component.

While the electrochemical based ion and small molecule detector of the present invention preferably uses zeolites as the active ion-exchange component, those skilled in the art will recognize that other ion-exchange materials may be used with pores having an appropriate size distribution relative to the species the system is designed to detect. For example the materials used in ion-exchange columns may be encapsulated into an electrode arrangement by mixing with a suitable conducting component and using a suitable binder to immobilize the mixture on an electrode. Since both positively and negatively charged ion-exchange materials are readily available, both cation and anion electrochemical detectors could be fabricated based on these ion-exchange materials.

Numerous experimental studies confirming the efficacy of the detector of the present invention for detecting ions and water have been carried out. The results of three of these studies will now be presented. It will be appreciated that the detection regimes used as examples here do not reflect the ultimate detection limits achievable for the detector electrode.

EXPERIMENTAL STUDIES

1. Ion Detector

The zeolite detector used in both modes (ion and water sensor) used silver as the electroactive species. The $Ag^+$ containing detector electrode was prepared by ion exchanging about 1 gram of zeolite Y (ion detector) zeolite A (water detector) using a solution of 0.01M silver nitrate. Following an overnight exchange, the zeolite sample was carefully washed, air dried, lightly ground to a fine powder and stored over saturated ammonium chloride solution.

The procedure used to fabricate the electrodes comprised lightly grinding about 100 mg of the ion exchanged zeolite. This was then dispersed in a solution of tetrahydrofuran (THF) containing 10 mg of polystyrene and then vigorously stirred. Using a micro-pipette, 20 microlitre aliquots of this solution were then applied to conductive indium tin oxide (ITO) coated glass blanks (Donnely-Meirs Corp., Mich.) which served as the conducting substrate of the working electrode. The electrode was then air dried. The weight of the electrode coating was typically about 1.5 mg.

Figure 10:
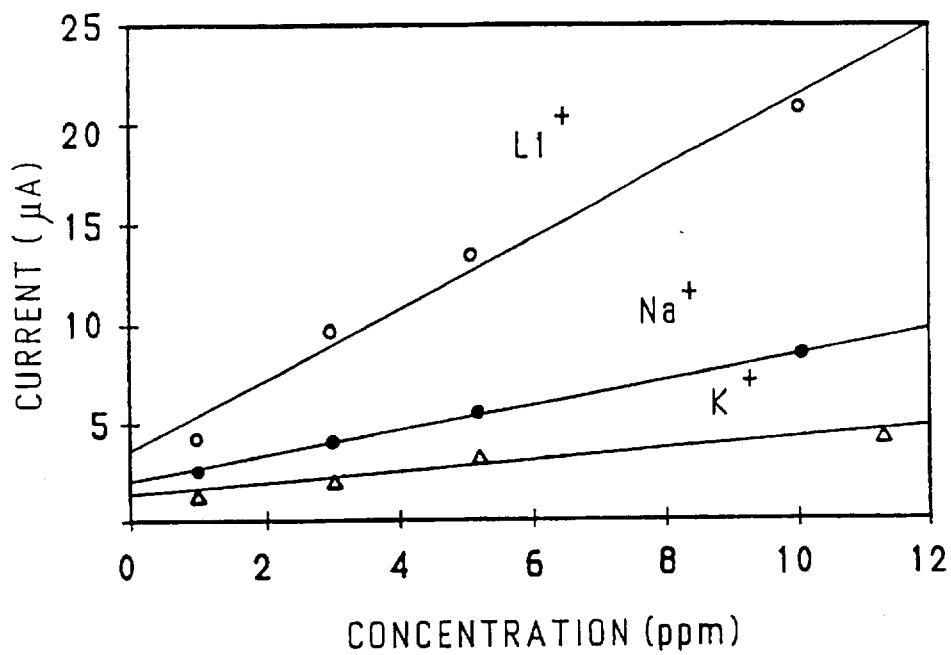
FIG. 10 illustrates experimental data recorded using the detector electrode as an ion detector for the detection of $K^+$, $Na^+$ and $Li^+$ in 0.10M tetrabutylammonium perchlorate in methanol/$H_2O$ with silver as the electroactive species.

A 0.10M tetrabutylammonium perchlorate in methanol/$H_2O$ was prepared. The detector electrode was then tested by standard addition of various cations as shown in FIG. 10. These data clearly shown the efficacy of the detector for detecting ionic species in solution.

2. Water Detector

Figure 11:
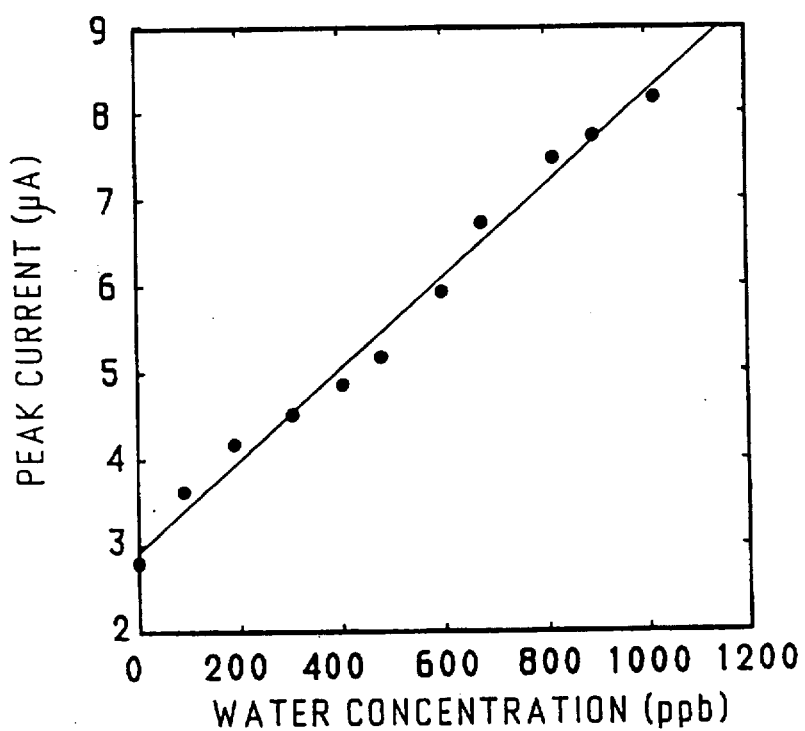
FIG. 11 shows a calibration curve constructed using data obtained in a standard addition experiment in an electrolyte of 0.1M $LiClO_4$ in dry dimethylformamide.

The zeolite detector electrode containing silver was fabricated in essentially the same manner as described above. A solution of 0.10M lithium perchlorate in n,n-dimethyl formamide was prepared. The solvent glassware etc. and supporting electrolyte were thoroughly dried before use. All experimentation was performed in a Vacuum Atmospheres dri-box. FIG. 11 illustrates the response of the detector electrode to trace concentrations of water in a standard addition experiment. These data clearly show the efficacy of the detector for detecting water in organic liquids, between 100 and 1,000 ppb.

Figure 12:
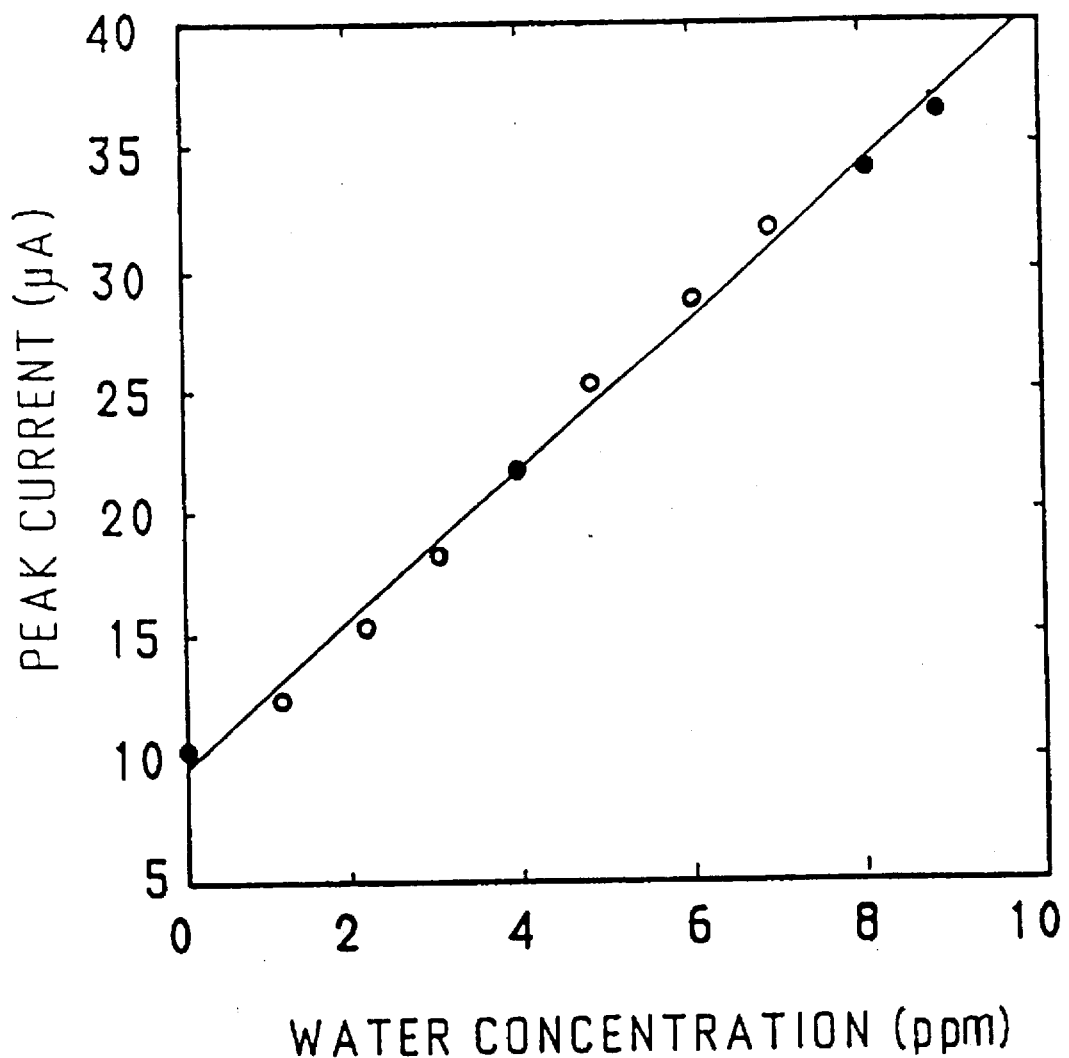
FIG. 12 shows a calibration curve constructed using data obtained in a standard addition experiment in an electrolyte of 0.1M $LiClO_4$ in dry dimethylformamide.

With reference to FIG. 12 it is also shown that in the same solvent water can be detected from 1–9 ppm. This is also the result of a standard addition experiment.

Note that these data are the result of anodic stripping experiments. In these experiments the electrode was held at a potential negative of the reversible potential of silver for a period of time during which silver was ion exchanged and plated onto the conducting portion of the detector electrode. After a certain period of time the detector electrode potential was scanned positively and the plated silver stripped. Referring to FIGS. 10–12, it is evident the detector will operate in the sub ppm range for both water and cations.

There are numerous techniques available to increase the detection limit of the ion and water sensitive detector of the present invention. Those skilled in the art will appreciate that various AC techniques as well as pulsed voltammetry are available for improving the detection limit of DC voltammetry through the suppression of charging currents. In addition, the fact that the anodic waves for the water sensor discussed above are stripping peaks means that this sensor can operate in a manner similar to stripping analysis in polarography. This is the most sensitive electroanalytical technique so far developed and detection limits for many analytes less than 0.01 ppb are routine.

While the method of detecting electroinactive ions and electroinactive ions solvated by small molecules forming the subject invention has been described and illustrated with respect to the preferred embodiments, it will be appreciated by those skilled in the art that numerous variations of these embodiments may be made without departing from the scope of the invention disclosed herein.

Therefore what is claimed is:

1. A method for detecting electroinactive ions or electroinactive ions solvated by small molecules in aqueous liquid samples, comprising the steps of:

a) providing an aqueous liquid sample to be tested for electroinactive ions or small molecules and contacting said aqueous liquid sample with zeolite having pores of molecular dimensions effective for restricting access to the pores on the basis of size, said pores initially containing electroactive ions within said pores, whereby at least some of said electroactive ions are released into the aqueous liquid sample from said pores by ion exchange with electroinactive ions or electroinactive ions solvated by small molecules when the electroinactive ions or electroinactive ions solvated by small molecules can access the pores on the basis of size;

b) bringing the aqeuous liquid sample containing said electroactive ions into contact with an electrode after the aqueous liquid sample has contacted said zeolite, and applying a bias potential to the electrode with respect to a counter-electrode whereby the bias potential is sufficient to cause an electrochemical reaction between the electroactive species and the electrode to produce an electrical current; and c) recording the electrical current resulting from the electrochemical reaction.

2. The method according to claim 1 including the step of relating said electrical current to a concentration of the electroinactive ions in said aqueous liquid sample.

3. The method according to claim 2 wherein said aqueous liquid sample is continuously flowed through a flow system containing the zeolite and the electrode, the aqueous liquid sample first being flowed into contact with the zeolite and then past the electrode.

4. A method for detecting impurity small molecules in organic solvents comprising organic molecules and electroinactive ions, comprising the steps of:

a) providing a sample of an organic solvent to be tested for impurity small molecules contained therein and contacting said sample with a zeolite having pores of molecular dimensions effective for restricting access to the pores on the basis of size, said pores initially containing electroactive ions within said pores, whereby at least some of said electroactive ions are released into the sample from said pores by ion exchange with electroinactive ions solvated by impurity small molecules when the electroinactive ions solvated by small molecules can access the pores on the basis of size; thereafter b) bringing the sample containing said electroactive ions into contact with an electrode and applying a bias potential to the electrode with respect to a counter-electrode whereby the bias potential is sufficient to cause an electrochemical reaction between the electroactive species and the electrode to produce an electrical current; and c) recording the electrical current resulting from the electrochemical reaction.

5. The method according to claim 4 wherein water is the impurity small molecule being tested for, wherein said electroinactive ions solvated by impurity small molecules is electroinactive ions hydrated by water molecules.

6. The method according to claim 5 wherein said zeolite is zeolite A.

7. The method according to claim 5 wherein said sample is continuously flowed through a flow system containing the zeolite and the electrode, the sample first being flowed into contact with the zeolite and then past the electrode.

8. The method according to claim 4 including the step of relating said electrical current to a concentration of the electroinactive ions in said sample.

* * * * *